United States Patent [19]
Kobayashi

[11] Patent Number: 6,063,486
[45] Date of Patent: May 16, 2000

[54] MOISTURE SENSOR COMPRISING CONDUCTIVE PARTICLES AND A HYGROSCOPIC POLYMER OF POLYVINYL ALCOHOL

[75] Inventor: Nobuo Kobayashi, Tokyo, Japan

[73] Assignee: TDK Corporation, Tokyo, Japan

[21] Appl. No.: 08/982,890

[22] Filed: Dec. 2, 1997

[30] Foreign Application Priority Data

Dec. 10, 1996 [JP] Japan ................................. 8-346747

[51] Int. Cl.[7] .................................................. B32B 5/16
[52] U.S. Cl. ............................................. 428/323; 338/35
[58] Field of Search .......................... 338/34, 35; 34/528; 428/323, 913

[56] References Cited

U.S. PATENT DOCUMENTS

| | | | |
|---|---|---|---|
| 3,983,527 | 9/1976 | Ohsato et al. ........................... | 338/35 |
| 4,520,341 | 5/1985 | Miyoshi et al. .......................... | 338/35 |
| 4,562,725 | 1/1986 | Oka et al. ................................ | 73/29 |
| 4,629,677 | 12/1986 | Katoh ...................................... | 430/215 |
| 4,632,879 | 12/1986 | Tanaka et al. ........................... | 428/522 |
| 4,760,368 | 7/1988 | Sugihara et al. ......................... | 338/34 |
| 5,066,563 | 11/1991 | Aono et al. .............................. | 430/213 |
| 5,085,980 | 2/1992 | Aono et al. .............................. | 430/531 |

*Primary Examiner*—Hoa T. Le
*Attorney, Agent, or Firm*—Oblon, Spivak, McClelland, Maier & Neustadt, P.C.

[57] ABSTRACT

A moisture sensitive film having conductive particles dispersed in a hygroscopic polymer is disposed between a pair of electrodes to construct a moisture sensor. The hygroscopic polymer is a modified polyvinyl alcohol which is obtained by saponifying a polymer comprising vinyl ester units and 0.1 to 15 mol % of ethylenically unsaturated carboxylic acid units such that the vinyl ester units are saponified to a degree of at least 30 mol %. The moisture sensor has improved condensing/drying cycle performance and moisture resistance.

3 Claims, 1 Drawing Sheet

MOISTURE SENSOR COMPRISING CONDUCTIVE PARTICLES AND A HYGROSCOPIC POLYMER OF POLYVINYL ALCOHOL

This invention relates to a moisture sensor comprising a moisture sensitive film having conductive particles dispersed in a hygroscopic polymer.

BACKGROUND OF THE INVENTION

One class of well-known moisture sensors for sensing humidity and moisture condensation includes moisture sensors comprising a moisture sensitive film having conductive particles dispersed in a hygroscopic polymer as disclosed in JP-A 99740/1983, 170755/1984, 250241/1985, 21052/1987, and 249813/1994.

Among these, JP-A 21052/1987 discloses the use of polyvinyl alcohol (PVA, also known as POVAL) as the hygroscopic polymer. This sensor is insufficient in sensitivity and condensing/drying cycle performance. As an improvement over this sensor, JP-A 249813/1994 discloses a polyvinyl alcohol having a degree of saponification of 60 to 95%, carbon black having a specific surface area of 80 to 800 $m^2/g$ as the conductive particles, and a moisture sensitive film having a thickness of less than 5.0 μm.

The condensing/drying cycle performance is not satisfactorily improved by using such a partially saponified polyvinyl alcohol. Polyvinyl alcohols including partially saponified ones must be crosslinked when they are actually used in moisture sensors. After the crosslinking treatment, however, some properties including condensing/drying cycle performance are significantly exacerbated, particularly in the case of JP-A 249813/1994.

SUMMARY OF THE INVENTION

An object of the invention is to provide a novel and improved moisture sensor having effective condensing/drying cycle performance and satisfactory moisture resistance.

The present invention provides a moisture sensor comprising a moisture sensitive film having conductive particles dispersed in a hygroscopic polymer between a pair of electrodes. The hygroscopic polymer is a modified polyvinyl alcohol which is obtained by saponifying a polymer comprising vinyl ester units and 0.1 to 15 mol % of ethylenically unsaturated carboxylic acid units such that the vinyl ester units are saponified to a degree of at least 30 mol %. Preferably, the moisture sensitive film has been crosslinked. Carbon black having a specific surface area of 30 to 300 $m^2/g$ is often used as the conductive particles.

BRIEF DESCRIPTION OF THE DRAWINGS

The only figure.

DETAILED DESCRIPTION OF THE INVENTION

Figure 1:
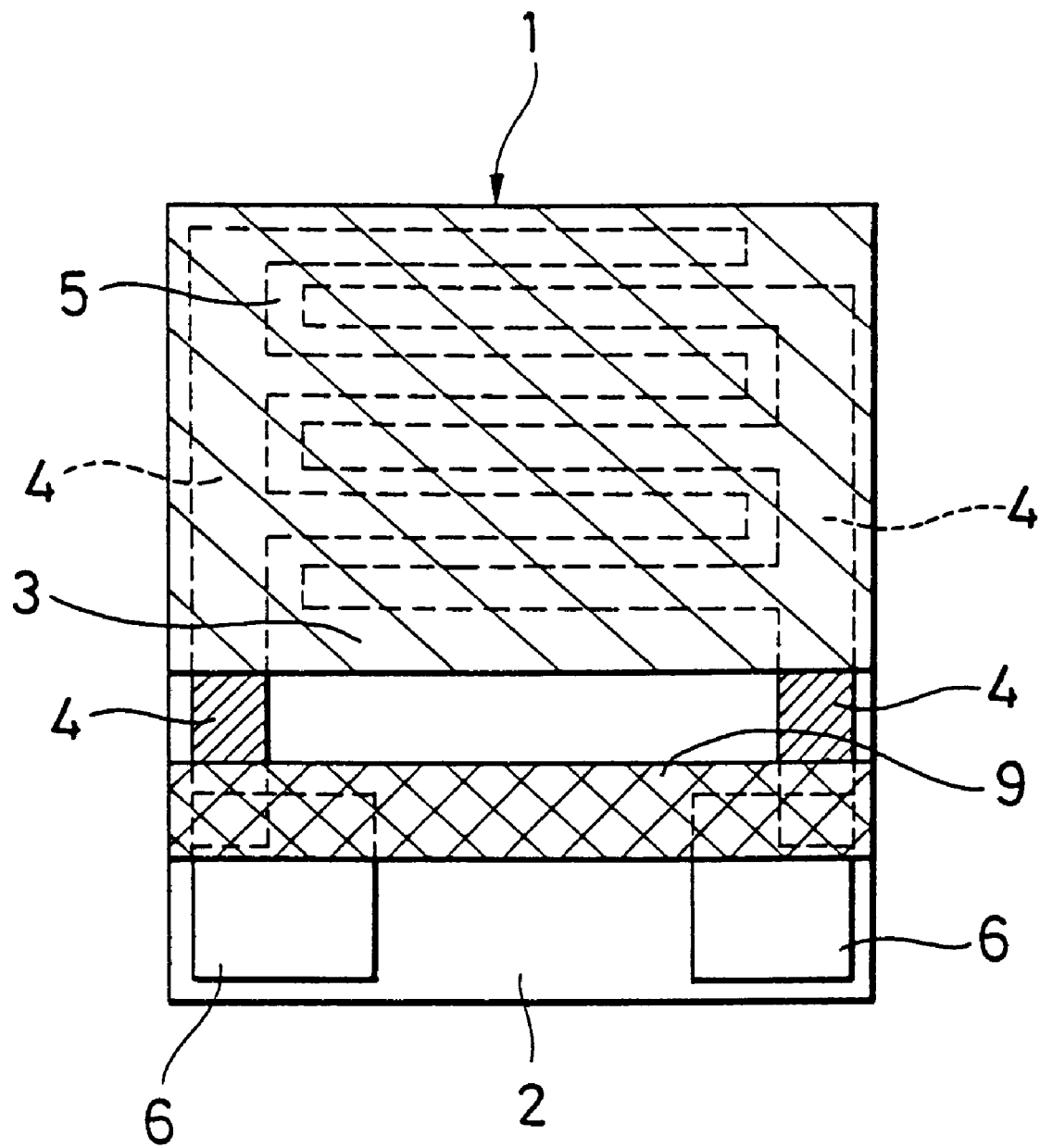
FIG. 1 is a schematic plan view showing a moisture sensor according to one embodiment of the invention.

The moisture sensor of the invention is typically used as a moisture condensation sensor and thus intended to sense a humidity in the range of about 95% to about 100% in relative humidity (RH).

In the moisture sensor of the invention, a modified polyvinyl alcohol which is obtained by saponifying a polymer comprising vinyl ester units and ethylenically unsaturated carboxylic acid units is used as the hygroscopic polymer. This modified polyvinyl alcohol contains 0.1 to 15 mol % of ethylenically unsaturated carboxylic acid units. The degree of saponification of the vinyl ester units is 30 mol % or higher.

The use of such a modified polyvinyl alcohol ensures the manufacture of a moisture sensor which exhibits effective condensing/drying cycle performance even after crosslinking treatment. The objects of the invention are not achieved if the content of ethylenically unsaturated carboxylic acid units is less than 0.1 mol %. A modified polyvinyl alcohol containing more than 15 mol % of ethylenically unsaturated carboxylic acid units is less soluble in water and becomes difficult to form a film. A degree of saponification of less than 30 mol % indicates a less number of hydroxyl groups in a molecule, which provides an insufficient increase of resistance upon contact with moisture to function as the moisture sensor.

Better results are obtained when the content of ethylenically unsaturated carboxylic acid units is 0.1 to 10 mol % and/or when the degree of saponification is 30 to 100 mol %, more preferably 50 to 100 mol %, especially 60 to 99.9 mol %.

The modified polyvinyl alcohol (PVA) used herein is obtained by saponifying a copolymer of a vinyl ester and an ethylenically unsaturated carboxylic acid.

Examples of the vinyl ester include vinyl acetate, vinyl propionate, and vinyl formate, with the vinyl acetate being often used. Examples of the ethylenically unsaturated carboxylic acid include ethylenically unsaturated monocarboxylic acids such as acrylic acid, methacrylic acid, and crotonic acid, and ethylenically unsaturated dicarboxylic acids such as itaconic acid, maleic acid, fumaric acid, glutaconic acid, and allylmalonic acid. Also included are monomers capable of generating a carboxyl group through saponification, for example, esters of the aforementioned ethylenically unsaturated carboxylic acids and acid anhydrides such as itaconic anhydride and maleic anhydride. Preferred among others are ethylenically unsaturated dicarboxylic acids such as itaconic acid, maleic acid, and fumaric acid.

In addition to units originating from the vinyl ester and the ethylenically unsaturated carboxylic acid, the modified polyvinyl alcohol used herein may contain units originating from another monomer. Examples of the comonomer include olefins such as ethylene, olefins having 3 to 5 carbon atoms, and olefins having 8 to 18 carbon atoms; vinyl carboxylates such as vinyl Versatate (=Versatic Acid ester) and vinyl stearate; alkyl vinyl ethers such as lauryl vinyl ether and methyl vinyl ether; methacrylates such as methyl methacrylate; acrylamides such as acrylamide, methacrylamide, and N,N-dimethylacrylamide; sulfonic acid monomers such as vinyl sulfonate and acryl sulfonate; cationic monomers such as dimethylaminoethyl methacrylate, vinyl imidazole, vinyl pyridine, and vinyl succinimide; and vinylene carbonate, allyl alcohol and allyl acetate. The content of such additional monomer units is less than 15 mol %, preferably less than 10 mol %.

Since lower crystallinity is preferred for the modified polyvinyl alcohol used herein, it preferably contains units originating from a bulky monomer. Such monomers are vinyl Versatate, vinyl stearate and lauryl vinyl ether.

The vinyl ester, ethylenically unsaturated carboxylic acid and other monomer which are used to form the modified polyvinyl alcohol may be used alone or in admixture of two or more. If desired, there may be employed in combination a method of modifying the polyvinyl alcohol by secondarily reacting it with a compound which is reactive with a hydroxyl group of the polyvinyl alcohol.

Illustrative, non-limiting examples of the modified polyvinyl alcohol used herein are given below. They are expressed by a combination of starting monomers.

1) vinyl acetate/itaconic acid (95.1–99.1/4.9–0.9 mol %) degree of saponification 65–99.5 mol %
2) vinyl acetate/maleic acid (98.5–98.9/1.5–1.1 mol %) degree of saponification 96–99.1 mol %
3) vinyl acetate/fumaric acid (98/2 mol %) degree of saponification 99.3 mol %
4) vinyl acetate/crotonic acid (94.7–98/5.3–2 mol %) degree of saponification 90 mol %
5) vinyl acetate/acrylic acid (96.6/3.4 mol %) degree of saponification 93 mol %
6) vinyl acetate/dimethyl itaconate (95.4–98.9/4.6–1.1 mol %) degree of saponification 77–88 mol %
7) vinyl acetate/maleic anhydride (96.5/3.5 mol %) degree of saponification 88–95 mol %
8) vinyl acetate/methyl acrylate (96.3/3.7 mol %) degree of saponification 93 mol %
9) vinyl acetate/methyl methacrylate (95.0–98.2/5.0–1.8 mol %) degree of saponification 86–99.5 mol %
10) vinyl acetate/monomethyl maleate (99.5/0.5 mol %) degree of saponification 99.6 mol %
11) vinyl acetate/itaconic acid/vinyl Versatate (90.0–98.0/6.0–1.0/4.0–1.0 mol %) degree of saponification 97.8–99.1 mol %
12) vinyl acetate/maleic anhydride/heptene (97.0/1.0/2.0 mol %) degree of saponification 97.8–99.1 mol %
13) vinyl acetate/maleic anhydride/stearyl vinyl ether (97.8/1.0/1.2 mol %) degree of saponification 97.8–99.1 mol %
14) vinyl acetate/maleic anhydride/octyl acrylamide (96.0/1.0/3.0 mol %) degree of saponification 97.8–99.1 mol %
15) vinyl acetate/itaconic acid/ally acetate (90.5/0.45/0.5 mol %) degree of saponification 60.8 mol %

In connection with these modified polyvinyl alcohols, the degree of saponification is that of the vinyl ester. Substantially the entire amount of the carbonyl group contained in the acid anhydride or vinyl acid ester takes the form of a carboxyl group or a carboxylate salt such as Na salt.

The modified polyvinyl alcohols of the invention usually have a degree of polymerization of about 100 to about 3,000.

The modified polyvinyl alcohols of the invention can be synthesized by the methods described in Nagano, Yamane and Toyoshima, "POVAL," Kobunshi Kankokai, 1970, and the literature cited therein, for example, JP-A 111189/1978, 82808/1981, and 128265/1984.

In the practice of the invention, only one modified polyvinyl alcohol is usually employed although a mixture of two or more modified polyvinyl alcohols may be used in some cases.

The conductive particles used herein include carbon particles such as carbon black and graphite and metal powders such as nickel and copper powders. Carbon black is typically used. Preferred carbon black has a specific surface area of 30 to 300 $m^2/g$, more preferably 30 to 150 $m^2/g$, especially 30 to 75 $m^2/g$. Further preferably, primary particles of carbon black have a mean particle diameter of 20 to 50 nm, a well developed structure, and a DBP oil absorption of at least 100 ml/100 g, typically 100 ml/100 g to 150 ml/100 g. In general, conductive particles have a mean particle diameter of about 20 nm to about 3 $\mu$m (for non-spherical particles, the diameter of a circle equivalent to the projected area).

The amount of conductive particles filled in the moisture sensitive film is preferably 10 to 50% by weight, more preferably 15 to 40% by weight in the case of carbon black. A too low packing density of conductive particles would lead to a too high resistance value in a dry state. With a too high packing density of conductive particles, no substantial increase of resistance would occur upon moisture condensation, failing to detect moisture condensation. The amount of other conductive particles may be analogous to that of carbon black.

It is preferred for practical use to crosslink the moisture sensitive film containing the above-mentioned components because moisture resistance is improved. Crosslinking is typically carried out using crosslinking agents. Those crosslinking agents used in the crosslinking of polyvinyl alcohol are useful. Exemplary crosslinking agents include aldehydes such as glyoxal, dialdehydes like sulfur-containing dialdehydes, both end aldehyde-bearing poval, side chain aldehydes, dialdehyde starch, and polyacrolein; methylol compounds such as N-methylolurea and N-methylolmelamine; active vinyl compounds such as divinyl sulfone and bis($\beta$-hydroxyethylsulfone); epoxy compounds such as epichlorohydrin, glycidyl methacrylate, diglycidyl ether, and epoxidized polyamide polyamines; polycarboxylic acids and diisocyanates; and inorganic crosslinking agents. Preferred among these are N-methylolmelamine, diglycidyl ether, and epoxidized polyamide polyamines. The amount of the crosslinking agent added is preferably about 1 to 50% by weight of the modified polyvinyl alcohol. Ultraviolet and radiation crosslinking may also be used.

Any desired method may be used to form the moisture sensitive film. Typically, it is formed by coating a dispersion containing the above-mentioned components. The dispersing medium is preferably water or a mixture of water and a hydrophilic solvent. Screen printing is a typical coating technique.

After a coating is formed, it is dried at a temperature of about 80 to 150° C. for about ½ to 3 hours. When a crosslinking agent is contained, drying also causes the crosslinking of the coating.

The resulting moisture sensitive film preferably has a dry thickness of up to 5.0 $\mu$m, especially 1 to 3.5 $\mu$m. This range of thickness ensures sufficient moisture permeation.

The structure of the moisture sensor is not critical insofar as it has the moisture sensitive film between a pair of electrodes.

One exemplary structure of the moisture sensor is shown in FIG. 1. The moisture sensor generally designated at 1 includes an insulating substrate 2 and a pair of comb-shaped electrodes 4 thereon. The pair of comb-shaped electrodes 4 are arranged on the substrate 2 so that they interdigitate with each other via a gap 5 of a predetermined distance. A moisture sensitive film 3 is formed on the insulating substrate 2 and comb-shaped electrodes 4. A terminal 6 is connected to one end of each electrode 4. A resist film 9 may be provided as shown in the figure. The gap between the air of electrodes is typically about 100 to 500 $\mu$m.

With the illustrated construction, a voltage is applied between the electrodes. Since the moisture sensitive film changes its resistance in proportion to a humidity, the humidity is detected from a change of output voltage.

In the illustrated construction, the insulating substrate 2 is made of any desired electrically insulating material which firmly joins with the moisture sensitive film 3, for example, glass, plastics, ceramics and insulating layer-coated metal.

The electrodes 4 are made of any commonly used material. For example, they are formed by screen printing a low resistance paste containing Au or $RuO_2$ and optionally glass frit, followed by high temperature sintering. The electrode terminals 6 are made of Ag-Pd alloy, for example, by printing a paste thereof in a conventional manner and baking at high temperature. The resist film 9 is formed of glass, for example, while its gage and shape are not critical.

The moisture sensor of the invention is not limited to the illustrated one and various structures are employable.

EXAMPLE

Examples of the invention are given below by way of illustration and not by way of limitation.

Examples 1–4

Four polymers P-1, P-2, P-3, and P-4 were selected as a hygroscopic polymer from modified polyvinyl alcohols (degree of polymerization 100 to 3,000) containing 0.45 to 6.0 mol % of ethylenically unsaturated carboxylic acid units and having a degree of saponification of vinyl acetate portion of 60.8 to 99.5 mol %. The composition of polymers P-1 to P-4 is shown below.
P-1: vinyl acetate/itaconic acid/vinyl Versatate (91.0/5.0/4.0 mol %), degree of saponification 98 mol %
P-2: vinyl acetate/maleic anhydride (96.5/3.5 mol %), degree of saponification 88 mol %
P-3: vinyl acetate/itaconic acid (95/5 mol %), degree of saponification 90 mol %
P-4: vinyl acetate/crotonic acid (97/3 mol %), degree of saponification 90 mol %

A moisture sensitive material paste was prepared by diluting each of polymers P-1 to P-4 with water to form a 15 wt % aqueous solution, adding 6 parts by weight of carbon black (Toka Black #4500, Tokai Carbon K.K., specific surface area 58 $m^2/g$), 40 parts by weight of an epoxy crosslinking agent (Arafix 100, Arakawa Chemical K.K.), and 2 parts by weight of n-hexyl alcohol as an antifoam agent to 100 parts by weight of the polymer solution, and dispersing them in an agitator (KK100, Kurabo K.K.).

The paste was applied onto a pair of comb-shaped electrodes of ruthenium oxide on an alumina substrate by screen printing and heated at 120° C. for one hour for drying and crosslinking, obtaining a moisture sensor of the structure shown in FIG. 1. The moisture sensitive film had a dry thickness of 3 $\mu m$. Moisture sensors of Examples 1 to 4 correspond to polymers P-1 to P-4, respectively.

Comparative Example 1

A moisture sensor was prepared by the same procedure as Examples 1 to 4 except that a moisture sensitive material paste was prepared by adding 6 parts by weight of Toka Black #4500 and 2 parts by weight of n-hexyl alcohol as an antifoam agent to 100 parts by weight of a 15 wt % aqueous solution of Polyvinyl Alcohol 420 (Kurare K.K., degree of saponification 79.5 mol %), followed by agitation.

Comparative Example 2

A moisture sensor was prepared by the same procedure as Examples 1 to 4 except that a moisture sensitive material paste was prepared by adding 6 parts by weight of Toka Black #4500, 40 parts by weight of Arafix 100 as a crosslinking agent, and 2 parts by weight of n-hexyl alcohol as an antifoam agent to 100 parts by weight of a 15 wt % aqueous solution of Polyvinyl Alcohol 420, followed by agitation.

Comparative Example 3

A moisture sensor was prepared by the same procedure as Examples 1 to 4 except that a moisture sensitive material paste was prepared by adding 6 parts by weight of carbon black (Carbon Black #5500, Tokai Carbon K.K., specific surface area 215 $m^2/g$) and 2 parts by weight of n-hexyl alcohol as an antifoam agent to 100 parts by weight of a 15 wt % aqueous solution of Polyvinyl Alcohol 224 (Kurare K.K., degree of saponification 88 mol %), followed by agitation.

Comparative Example 4

A moisture sensor was prepared by the same procedure as Examples 1 to 4 except that a moisture sensitive material paste was prepared by adding 4 parts by weight of acetylene black (specific surface area 202 $m^2/g$) and 2 parts by weight of n-hexyl alcohol as an antifoam agent to 100 parts by weight of a 15 wt % aqueous solution of Polyvinyl Alcohol 224, followed by agitation.

Comparative Example 5

A moisture sensor was prepared by the same procedure as Examples 1 to 4 except that a moisture sensitive material paste was prepared by adding 6 parts by weight of carbon black (Carbon Black #5500, Tokai Carbon K.K., specific surface area 215 $m^2/g$), 40 parts by weight of Arafix 100 as a crosslinking agent, and 2 parts by weight of n-hexyl alcohol as an antifoam agent to 100 parts by weight of a 15 wt % aqueous solution of Polyvinyl Alcohol 224 (Kurare K.K., degree of saponification 88 mol %), followed by agitation.

The moisture sensors were examined by the following tests, with the results shown in Table 1.

Each sensor was allowed to stand in an atmosphere of 25° C. and RH 0% for 10 minutes and then measured for resistance designated R1 (RH 0%). The sensor was allowed to stand at RH 100% for 10 minutes and then measured for resistance designated R (RH 100%). The humidity of the atmosphere was brought back to RH 0% and the sensor was measured for resistance after 10 minutes and 60 minutes.

The resistance measured after 10 minutes is R2 (RH 0%) and the resistance measured after 60 minutes is R3 (RH 0%). The values of R1, R2 and R3 were compared. The values of R2/R1 and R3/R1 are also shown in parentheses in the columns "R2" and "R3."

Moisture resistance was examined by allowing each sensor to stand in an atmosphere of 85° C. and RH 85% for 1,000 hours. It was examined whether the resistance vs. humidity relationship changed and whether the outer appearance of the moisture sensitive film changed before and after the moisture exposure test. The rating is made according to the following criterion.

⊚: no change of resistance vs. humidity

○: slight change of resistance vs. humidity

Δ: noticeable change of resistance vs. humidity

×: moisture sensitive film dissolved

It is noted that polyvinyl alcohol is abbreviated as PVA in Table 1.

TABLE 1

|  | Hygroscopic polymer | Crosslinking agent | Conductive particles (specific surface area) | R1 (RHO %) | R (RH 100%) | R2 (RHO %) [R2/R1] | R3 (RHO %) [R3/R1] | Moisture resistance |
|---|---|---|---|---|---|---|---|---|
| Example 1 | modified PVA: P-1 | occurred | carbon black #4500 (58 m²g) | 590 Ω | 15MΩ | 830 Ω [1.4] | 720 Ω [1.2] | ◉ |
| Example 2 | modified PVA: P-2 | occurred | carbon black #4500 | 510 Ω | 57MΩ | 970 Ω [1.9] | 770 Ω [1.5] | ◉ |
| Example 3 | modified PVA: P-3 | occurred | carbon black #4500 | 590 Ω | 140MΩ | 900 Ω [1.5] | 800 Ω [1.4] | ◉ |
| Example 4 | modified PVA: P-4 | occurred | carbon black #4500 | 600 Ω | 20MΩ | 790 Ω [1.3] | 740 Ω [1.2] |  |
| Comparison 1 | PVA420 (degree of saponification 79.5 mol %) | not | carbon black #4500 | 730 Ω | 13MΩ | 2.5 kΩ [3.4] | 2.0 kΩ [2.7] | X |
| Comparison 2 | PVA420 | occurred | carbon black #4500 | 660 Ω | 10MΩ | 1.5 kΩ [2.3] | 1.3 kΩ [2.0] | ○ |
| Comparison 3 | PVA224 (degree of saponification 88 mol %) | not | carbon black #5500 (215 m²g) | 600 Ω | 3.3MΩ | 1.2 kΩ [2.0] | 1.0 kΩ [1.7] | X |
| Comparison 4 | PVA224 | not | acetylene black #4500 (202 m²g) | 3.8 kΩ | 28MΩ | 75 kΩ [19.7] | 64 kΩ [16.8] | X |
| Comparison 5 | PVA224 | occurred | carbon black #5500 | 780 Ω | 14 kΩ | 1.6 kΩ [2.1] | 1.6 kΩ [1.9] | ○ |

It is evident from Table 1 that the moisture sensors within the scope of the invention (Examples 1 to 4) show resistances R2 and R3 after moisture condensation which are respectively suppressed to less than 1.9 times and less than 1.5 times as compared with resistance R1 before moisture condensation, and have high moisture resistance. In contrast, the moisture sensors of Comparative Examples 1 to 5 show R2 and R3 which are respectively more than 2 times and more than 1.7 times as compared with R1. The moisture sensor of Comparative Example 3 which was constructed as disclosed in JP-A 249813/1994 showed a relatively small change of resistance before and after moisture condensation, but was insufficient in moisture resistance because the moisture sensitive film had not been crosslinked. It is not acceptable on actual use. The moisture sensor of Comparative Example 5 which was constructed by adding a crosslinking agent to Comparative Example 3 showed an insufficient rise of resistance at RH 100% to use in practice.

There has been described a moisture sensor having effective condensing/drying cycle performance and satisfactory moisture resistance.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A moisture sensor comprising a moisture sensitive film having conductive particles dispersed in a hygroscopic polymer between a pair of electrodes, the hygroscopic polymer being a modified polyvinyl alcohol which is obtained by saponifying a polymer comprising vinyl ester units and 0.1 to 15 mol % of ethylenically unsaturated carboxylic acid units such that the vinyl ester units is saponified to a degree of at least 30 mol %.

2. The moisture sensor of claim 1 wherein the moisture sensitive film has been crosslinked.

3. The moisture sensor of claim 1 wherein said conductive particles are composed of carbon black having a specific surface area of 30 to 300 m²/g.

* * * * *